US00PP14957P2

(12) United States Plant Patent
Redman

(10) Patent No.: US PP14,957 P2
(45) Date of Patent: Jun. 29, 2004

(54) CHRYSANTHEMUM PLANT NAMED 'DRAGON TIME'

(50) Latin Name: *Chrysanthemum morifolium*
Varietal Denomination: Dragon Time

(75) Inventor: Ruth Redman, Bognor Regis (GB)

(73) Assignee: Cleangro LTD (GB)

( * ) Notice: Subject to any disclaimer, the term of this patent is extended or adjusted under 35 U.S.C. 154(b) by 0 days.

(21) Appl. No.: 10/652,195

(22) Filed: Aug. 29, 2003

(51) Int. Cl.[7] ..... A01H 5/00
(52) U.S. Cl. ..... Plt./286
(58) Field of Search ..... Plt./286

*Primary Examiner*—Anne Marie Grunberg
*Assistant Examiner*—June Hwu
(74) *Attorney, Agent, or Firm*—Howrey Simon Arnold & White, LLP

(57) ABSTRACT

A new variety of Chrysanthemum plant named 'Dragon Time,' having a full canopy of yellow and red single flowers. The new variety 'Dragon Time' has a medium to tall vigor with a free branching habit and a good foliage presentation.

1 Drawing Sheet

Latin name of the genus and species: Botanical classification: *Chrysanthemum morifolium.*

Variety denomination: The new Chrysanthemum variety denomination is 'Dragon Time.'

BACKGROUND OF THE INVENTION

The present invention comprises a new and distinct cultivar of Chrysanthemum botanically known as *Chrysanthemum morifolium,* and referred to by the cultivar name 'Dragon Time.'

'Dragon Time,' identified as 21612-0, originated from a cross made by Ruth Redman in a controlled breeding program in Vinnetrow Road, Chichester, West Sussex, United Kingdom. The female parent of the new variety is cultivar Machismo Time (U.S. Plant patent application Ser. No. 09/957,493). The male parent of the new variety is Swing Time Dark (U.S. Plant patent application Ser. No. 09/900,239). The new variety 'Dragon Time' has been asexually reproduced by vegetative cuttings in Chichester, West Sussex, United Kingdom and the distinguishing characteristics are retained through successive generations of asexual reproduction.

BRIEF SUMMARY OF THE INVENTION

'Dragon Time' is a pot type of Chrysanthemum plant variety having yellow and red bi-color single flowers.

Comparison with Female Parent

Plants of the new Chrysanthemum variety 'Dragon Time' are dissimilar to the parent cultivar in plant habitat and growth rate. In side-by-side comparisons in Chichester, West Sussex, United Kingdom, under commercial practice, plants of the new Chrysanthemum variety 'Dragon Time' differed from plants of the parent cultivar in the following characteristics.

1. The new variety 'Dragon Time' produces red and yellow single flowers whereas the parent cultivar produces brighter yellow and deeper red single flowers.
2. Plants of the new variety 'Dragon Time' have smaller and shorter inflorescence than plants of the parent cultivar.

3. The new variety 'Dragon Time' has a quicker response time than the plants of 'Machismo Time.'

Comparison with Male Parent

Plants of the new Chrysanthemum variety 'Dragon Time' are dissimilar to the parent cultivar in plant habitat and growth rate. In side-by-side comparisons in Chichester, West Sussex, United Kingdom, under commercial practice, plants of the new Chrysanthemum variety 'Dragon Time' differed from plants of the parent cultivar in the following characteristics.

1. The new variety 'Dragon Time' produces yellow and red single flowers whereas the parent cultivar produces deep orange single flowers.
2. Plants of the new variety 'Dragon Time' have larger and taller inflorescence than plants of the parent cultivar.

Comparison with Other Varieties

Plants of the new Chrysanthemum variety 'Dragon Time' are similar to the cultivar (U.S. Plant patent application Ser. No. 10/622,678) in plant habitat and growth rate. However, in side-by-side comparisons in Chichester, West Sussex, United Kingdom, under commercial practice, plants of the new Chrysanthemum variety 'Dragon Time' differed from plants of the cultivar in the following characteristics.

1. The new variety 'Dragon Time' produces yellow and red single flowers whereas the cultivar 'Nirvana Improved' also produces yellow and red single flowers.
2. Plants of the new variety 'Dragon Time' have smaller and shorter inflorescence than plants of the cultivar 'Nirvana Improved.'
3. Plants of the new variety 'Dragon Time' respond faster than plants of the cultivar 'Nirvana Improved.'

BRIEF DESCRIPTION OF ILLUSTRATION

Typical specimens of the plant and flowers for the new Chrysanthemum variety 'Dragon Time' are shown in the accompanying digital photograph. The colors shown are as true as possible within the usual limits of this kind of illustration.

FIG. 1 is a whole plant view of the new variety 'Dragon Time' grown in a pot. The plant shown in the illustration is 54 days from the commencement of Short Days.

DETAILED BOTANICAL DESCRIPTION

The following description of the new Chrysanthemum variety 'Dragon Time' is of plants grown in a greenhouse in Chichester, West Sussex, United Kingdom in the month of July. The cultivar has not been observed under all possible environmental conditions. The phenotype may vary significantly with variations in the environment such as temperature, length of day and light intensity, without any variance in genotype. The commercial classification of the new variety is a pot Chrysanthemum.

Plants of the new variety have been grown successfully under temperature conditions averaging about 19° C. at night and about 17° C. to 24° C. during the day under light conditions of about 5,000 to 6,000 foot candles. The plants respond well to the use of growth retardant, such as one B9 treatment at about 2 gm per liter. To produce a commercial product the plants may be pinched once with the center bud removed. The typical container size for commercial growth is 1 liter. It has been observed that the shelf life of the new variety is about 25 days with a response time of about 7 weeks. The new variety is suitable for growth in a temperature range of 15° C. to 25° C.

The new variety may be produced as a spray. The following description is with respect to a plant produced as pot. In the description of this new Chrysanthemum variety, color values have been taken from The Royal Horticultural Society Colour Chart (R.H.S.C.C.).

Plant

Plant type: Pot.
Habit: Upright.
Height: 22 cm.
Width: 33 cm.
Branching characteristics: Upright and free branching.
Length of lateral branches: 15 cm.
Number of breaks from pinch: 5.
Stem color: 137C.
Response time: 47 days.
Vigor: Medium/tall.
Shelf life: 25 days.
Disease (susceptibility or resistance): None observed.
Pest (susceptibility or resistance): None observed.
Drought or temperature resistance: None observed.
Growth retardant type and treatment: 3 applications of 2.5 gm/liter B9 @ 2, 21 and 28 days after sticking of unrooted cuttings. The plants were grown for 2 weeks in Long Day conditions (20 hours of light) and then transferred to Short Day conditions (13 hours of dark).
Propagation:
- *Type.*—Vegetative Propagation Via Stem Cuttings.
- *Time to rooting.*—14 days with soil temperatures of 18° C.
- *Rooting habit.*—After 7 days the first roots emerge and form root primordia. In 14 Long Days a complete root system is developed.

Foliage

Number of leaves per lateral branch: 12.
Compound or single: Single.
Arrangement of leaves: Alternate.
- *Shape of leaf.*—Typically 5 lobed.
- *Size of leaf.*—Width (cm): 3 to 5. Length (cm): 5.5 to 8.
- *Leaf apex.*—Acute.
- *Base.*—Obtuse.
- *Attachment.*—Petioled.
- *Aspect.*—Slightly undulating.
- *Margin.*—Lobed.
- *Surface characteristics.*—Top: slightly pubescent. Bottom: pubescent.

Petiole:
- *Color.*—137C.
- *Length.*—1.5 cm.

Venation: Net, prominent mid vein at underside.
- *Color.*—Upper side: 138C. Under side: 138C.

Color:
- *Mature leaf, upper side.*—Near 137A; under side: near 138A.
- *Young leaf, upper side.*—Near 147A; under side: near 137B.

Flower

Flower appearance: Matte.
Flower type: Single.
Flower form: Slightly cupped.
Flower shape: Round.
Flowering habit: Cyme.
Number of blossoms per branch: 7.
Inflorescence form: Cyme.
- *Depth of fully expanded blossoms.*—2 cm.
- *Diameter of fully expanded blossoms.*—7 cm.

Phyllaries:
- *Number.*—25.
- *Color.*—138B.
- *Length.*—0.9 cm.
- *Width.*—0.2 cm.
- *Texture/appearance.*—Pubescent.

Peduncle:
- *Length.*—14 cm (average).
- *Color.*—137C.
- *Surface.*—Slightly pubescent.
- *Habit.*—Slightly undulating.
- *Strength.*—Medium.

Pedicel:
- *Length.*—Terminal: 3.5 cm; lateral: 4 cm.
- *Color.*—137C.
- *Surface.*—Slightly pubescent.
- *Habit.*—Slightly undulating.
- *Strength.*—Medium.

Ray florets:
- *Form/shape.*—Oblong.
- *Texture/appearance.*—Matte.
- *Number per flower.*—36.
- *Length.*—4 cm; Width: 1 cm.
- *Apex.*—Rounded.
- *Base.*—Tapered.
- *Margin.*—Entire.

Disc florets:
- *Form/shape.*—Cylindrical.
- *Texture/appearance.*—Shiny.
- *Number per flower.*—300.
- *Length.*—0.6 cm; Width: 0.1 cm.
- *Diameter of disc.*—1.4 cm.

Fragrance: None observed.
Flower bud (at onset of color):
- *Length.*—1.4 cm.
- *Diameter.*—1.2 cm.
- *Form/shape.*—Globular.

General flower color:

1. *Ray florets, upper side.*—Immature: near 13A towards the apex and 44B from the center towards the base. Mature: near 13B towards the apex and 43B from the center towards the base. Older/Fading: near 13C towards the apex and 43C from the center towards the base.
2. *Ray florets, under side.*—Immature: near 12B towards the apex and 43B from the center towards the base. Mature: near 12C towards the apex and 43C from the center towards the base. Older/Fading: near 12C towards the apex and 43C from the center towards the base.
3. *Disc florets.*—Immature: near 144B. Mature: near 144C. Older/Fading: near 7C.
4. *Bud.*—12B and 44B.

Flower progression with age: There is no change with the flower form, but there is a slight color fading with age. Lastingness of the bloom is about 25 days.

Reproductive Organs

Gynoecium present on ray and disc florets:

*Pistil number on ray florets.*—36.

*Pistil number on disc florets.*—300.

*Stigma color.*—13A.

*Stigma shape.*—Forked.

*Style color.*—2B.

*Style length on ray florets.*—0.5 cm.

*Style length on disc florets.*—0.4 cm.

Androecium: Not observed on disc florets.

Fruit and seeds: None observed.

What is claimed is:

1. A new and distinct variety of Chrysanthemum plant, substantially as described and illustrated herein.

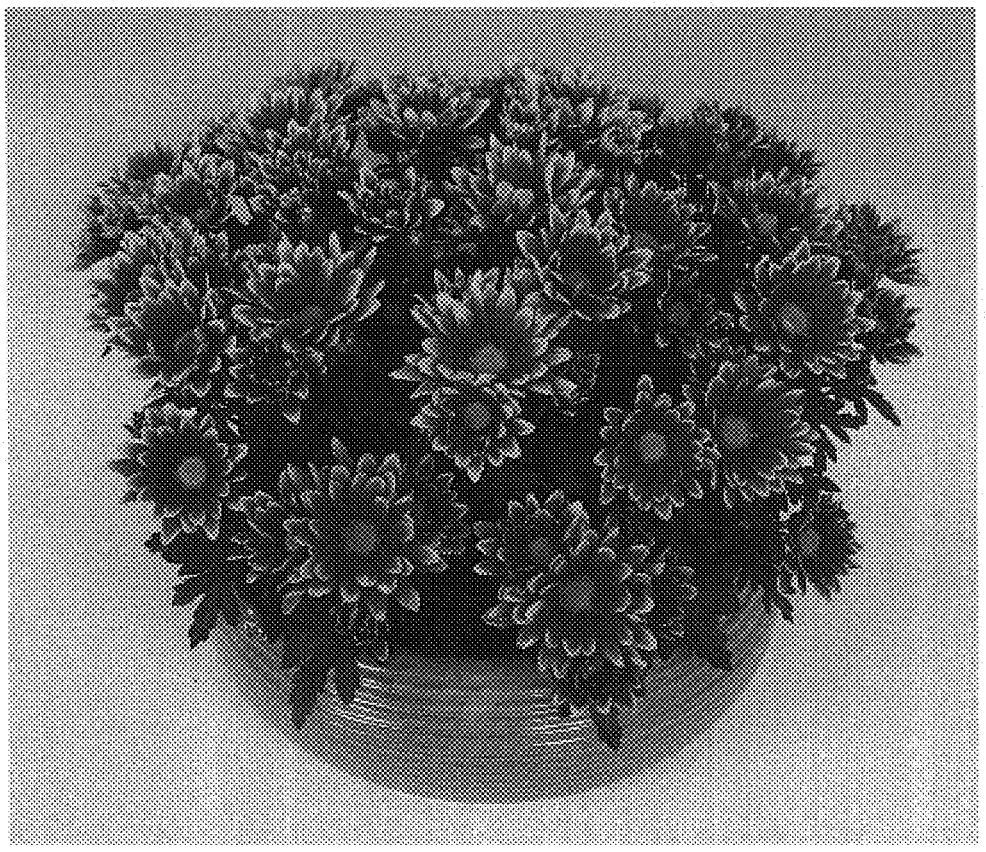

* * * * *